United States Patent
Kanade (10) Patent No.: US 12,419,533 B2
(45) Date of Patent: Sep. 23, 2025

(54) SYSTEM AND METHOD FOR ACQUIRING ELECTRICAL IMPEDANCE TOMOGRAPHY DATA

(71) Applicant: Udayan Kanade, Pune (IN)

(72) Inventor: Udayan Kanade, Pune (IN)

( * ) Notice: Subject to any disclaimer, the term of this patent is extended or adjusted under 35 U.S.C. 154(b) by 976 days.

(21) Appl. No.: 17/613,040

(22) PCT Filed: May 20, 2020

(86) PCT No.: PCT/IB2020/054807
§ 371 (c)(1),
(2) Date: Nov. 20, 2021

(87) PCT Pub. No.: WO2020/234813
PCT Pub. Date: Nov. 26, 2020

(65) Prior Publication Data
US 2022/0218226 A1   Jul. 14, 2022

(51) Int. Cl.
*A61B 5/0536* (2021.01)
*G01N 27/02* (2006.01)

(52) U.S. Cl.
CPC ......... *A61B 5/0536* (2013.01); *G01N 27/028* (2013.01); *A61B 2562/046* (2013.01)

(58) Field of Classification Search
CPC . A61B 5/0536; A61B 2562/046; A61B 5/053; G01N 27/028
See application file for complete search history.

(56) References Cited

U.S. PATENT DOCUMENTS

| | | | |
|---|---|---|---|
| 2006/0084859 A1* | 4/2006 | Johnson | A61B 5/7257 600/407 |
| 2011/0068861 A1* | 3/2011 | Denison | H03F 3/38 330/10 |
| 2012/0200302 A1* | 8/2012 | Wang | A61B 5/0536 324/600 |
| 2013/0006136 A1* | 1/2013 | Biancolillo | A61B 5/0535 600/547 |
| 2017/0042447 A1 | 2/2017 | Rossi | |
| 2019/0059777 A1* | 2/2019 | Aga | A61B 5/086 |

FOREIGN PATENT DOCUMENTS

WO   2012045188 A1   4/2012

* cited by examiner

*Primary Examiner* — Jason M Sims
*Assistant Examiner* — Kyle W. Kretzer (57) ABSTRACT

An AC current of multiple frequencies is setup in a body to be sensed, and amplitudes and phases of AC voltages at many electrodes attached to the body are detected simultaneously. At electrode measurement circuits, each of multiple modulating signals is mixed separately with the electrode signal using non-linear circuit components such as transistors or diodes. The output of this mixed signal is stored as a charge, in a capacitor or a semiconductor device (e.g. a CMOS transistor) that can store charge when in a certain state. Upon assertion of a readout signal, the charge is converted back into voltage and sent out on an analog voltage output line from which it is read using ADCs.

13 Claims, 10 Drawing Sheets

SYSTEM AND METHOD FOR ACQUIRING ELECTRICAL IMPEDANCE TOMOGRAPHY DATA

The present application is a US national stage application of international application no. PCT/IB2020/054807 filed on May 20, 2020, which claims priority from Indian patent application no. IN201921019798 titled "System and Method For Acquiring Electrical Impedance Tomography Data" filed in Mumbai, India on 20 May 2019.

TECHNICAL FIELD

The present invention is in the field of electrical impedance tomography. More specifically, the invention relates to electrical and electronic methods for acquiring electrical impedance tomography data from a plurality of electrodes.

BACKGROUND ART

Electrical impedance tomography is a technique of acquiring information about the interior of an electrically conductive body by sensing the body's electrical behavior on its surface. Usually, electric current is passed through the body at specified points, and voltage is measured across other points of the body. Many such readings are taken, each current changing the points at which current is introduced and/or the points at which voltages are measured. Many procedures or algorithms are used to gain information about the interior of the body from the above information.

The same basic technique with field specific modifications is known by various names, such as electrical impedance tomography, impedance tomography, bio-impedance tomography, electrical sounding, etc. Electrical impedance tomography may be used for medical or biological imaging (where the conductive body is the human/biological body, and information to be gained about the body includes information about internal organs, etc.), geophysical/ground surveys (where the conductive body is the Earth, and information to be gained about the body includes information about presence of water, oil, minerals, etc.) and non-destructive testing of machines, engineered bodies, civil constructions or materials (where the conductive body is the machine, civil structure/building, material sample etc., and information to be gained includes information about interior material presence, cracks, interior structure, etc.). It may also be used in applications such as archeology, forensic science, security, etc. where knowledge of the interior of a body without accessing the interior of the body is important.

SUMMARY OF INVENTION

In the present invention, an AC current of a particular frequency is setup in the body to be sensed, and amplitudes and phases of AC voltages at many (or all) electrodes attached to the body are detected simultaneously. This measurement is performed without requiring a tremendous number of A-to-D converters. Two modulating signals of the same frequency as the introduced AC current, one in phase with the AC input and one 90 degrees out of phase with it, are provided at all electrode measurement circuits. At the electrode measurement circuit, each of the mixing signals is mixed separately with the electrode signal. The mixing may be done using non-linear mechanisms such as transistors or diodes. The output of this mixed signal is stored as a charge, possibly in a capacitor or a semiconductor device (e.g. a CMOS transistor) that can store charge when in a certain state. Upon assertion of a readout signal, the charge is converted back into a voltage and sent out on an analog voltage output line. The charge is reset upon the assertion of a reset signal. Voltages are read out from the analog voltage lines using ADCs. The circuit asserts a few of the electrodes circuits at a time, so as to achieve maximum speed of readout while minimizing the number of ADCs required. Using sufficient integration time, noise is minimized. Furthermore, since the readouts are amplitudes and not AC waveforms, data transfer requirements are also reduced.

In an embodiment, the electrodes are arranged in a rectangular or hexagonal matrix. An entire row is integrated together, and asserted for readout together.

Advantageous Effects of Invention

A benefit of the present invention is the speed of acquiring tomographic information. Hundreds or thousands of data points are gathered simultaneously instead of one at a time. Furthermore, a relatively few number of ADC (analog-to-digital converter) circuits are required. This improvement in cost and data acquisition time allows acquisition of data across thousands of electrodes instead of the tens of electrodes that are usually employed in electrical impedance tomography. This allows much higher resolution and more accurate reconstruction of the interior of the body being sensed.

By using higher integration time, noise in measurements can be significantly reduced. Furthermore, the ADC directly converts data equivalent to amplitudes and phases of the sensed AC signals, rather than the AC signals themselves. This reduces the data rate required and the amount of post processing required. This also allows data from a higher number of electrodes to be gathered at more time instants.

BRIEF DESCRIPTION OF THE DRAWINGS

The following figures more particularly illustrate the invention.

DESCRIPTION OF EMBODIMENTS

The following embodiments more particularly describe the invention.

Figure 1:
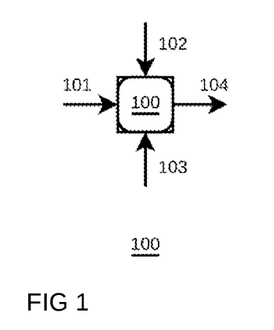
FIG. 1 illustrates a mixing sensor block, according to an embodiment.

FIG. 1 illustrates a mixing sensor block 100, according to an embodiment.

The mixing sensor block 100 is an electronic apparatus made up of electronic components. The mixing sensor block 100 has a sensing input line 101 that it senses the signal from. The mixing sensor block 100 has a modulating input line 102 that is used to input a modulating signal. The mixing sensor block 100 has an optional selection input line 103. The mixing sensor block 100 has an output line 104. In an embodiment, when the selection input line 103 is asserted, the mixing sensor block 100 produces a voltage corresponding to the sensed information on output line 104. If the selection input line 103 is not asserted, a high-impedance output is produced on output line 104. In this way, multiple output lines from multiple mixing sensor blocks may be ganged together and the signal may be passed to a single voltage sensor, which may be an analog to digital converter (ADC). In another embodiment, the selection input line 103 is not present, and signal is always presented on the output line 104. One out of many such signals produced by multiple mixing sensor blocks may be selected to pass to an ADC using a signal multiplexer.

We will now describe how the sensed information to be presented as voltage on the output line 104 is created. The signal on the sensing input line 101 and the signal on the modulating input line 102 are mixed with each other. This mixing may be any non-linear function of both the signals. In an embodiment, this non-linear function is or approximates a multiplication of the two signals. Such mixing of two signals may be achieved using non-linear circuit components such as diodes and transistors. Specific circuits such as imbalanced, balanced and doubly-balanced signal mixers may be used. In an embodiment, both the sensing input line 101 and the modulating input line 102 are voltage signals. This mixed signal is then filtered to select a particular frequency component of the signal, such as the DC or base-band component. The amplitude of this component is the information to be produced at the output, a voltage corresponding to which will be created on the output line 104 (when the selection input line is asserted, or always).

In an embodiment, this mixed signal is integrated for a certain amount of time using an integrating circuit component such as a capacitor (which may be a specifically created component, or may be an implicit capacitance of another semiconductor component such as a transistor). This integration achieves filtering to select the DC frequency, as well as reduction in noise. In an embodiment, extra signals are provided to the mixing sensor block 100. One such signal may expose or stop exposing the mixed signal to the integrating circuit component. Another such signal may reset the integrated signal to a standard value, to remove effects of previous use of the circuit.

In an embodiment, the modulating signal 102 is a sinusoidal signal. Such a sinusoidal signal may be produced using an oscillator circuit or ADC and provided to more than one mixing sensor blocks. In an embodiment, two modulating signals are available across the system of the present invention. Both these signals are at the same oscillating frequency, but they are out-of-phase with respect to each other by a certain amount (in an embodiment by 90 degrees). These signals may be present at the same time on two different circuits (or tracks), or may be present at different moments of operation of the present system.

Let the signal on the sensing input line 101 have multiple frequencies. This may be represented mathematically as $$x = x_1 e^{i\omega_1 t} + \bar{x}_1 e^{-i\omega_1 t} + \ldots + x_n e^{i\omega_n t} + \bar{x}_n e^{-i\omega_n t} \qquad \text{[Math. 1]}$$

where the frequencies occur in pairs of positive and corresponding negative frequencies, and the corresponding amplitudes are complex conjugates. Any signal x may be approximated as a sum of a multitude of such terms according to the theory of the Fourier transform. In the present invention, some of these signal components will be at frequencies deliberately introduced into the body being sensed, whereas other signal components may be stray noise. The signal on the modulating input line 102 is a single sinusoidal, which may be represented as $$y = y_1 e^{i\lambda t} + \bar{y}_1 e^{-i\lambda t} \qquad \text{[Math. 2]}$$

A mixer that multiplies these two signals produces the following signal $$xy = \left(\sum_i x_i e^{i\omega_i t} + \bar{x}_i e^{-i\omega_i t}\right)(y_1 e^{i\lambda t} + \bar{y}_1 e^{-i\lambda t}) \qquad \text{[Math. 3]}$$

which gives $$xy = \sum_i (x_i y_1 e^{i(\omega_i + \lambda)t} + \bar{x}_i y_1 e^{i(-\omega_i + \lambda)t} + x_i \bar{y}_1 e^{i(\omega_i - \lambda)t} + \bar{x}_i \bar{y}_1 e^{i(-\omega_i - \lambda)t}) \qquad \text{[Math. 4]}$$

A mixer may not precisely multiply the signal, but any mixer that creates a non-linear function of the two signals will have the above as components. We can choose a filter after the mixer such that only the frequency $\omega_i - \lambda$ (and its negative) remains in the output, and furthermore its amplitude is detected. In an embodiment, $\omega_i = \lambda$, so that $\omega_i - \lambda = 0$, and thus the signal detected is a DC signal. This signal can be preferentially extracted from other signals by using an integrator circuit (which may be a single capacitor), which will integrate the DC component which the various AC components cancel out.

Assuming $y_1$ is real (has a phase angle of zero) detected amplitude will be $$x_i y_1 + \overline{x_i} \overline{y_1} = 2y_1 \Re(x_i) \qquad \text{[Math. 5]}$$

This will allow us to detect the real part of the amplitude $x_i$. If we use a modulating signal that is 90 degrees out of phase with respect to this modulating signal y, it will produce a detected amplitude of $$\overline{x_i} iy_1 + x_i \overline{iy_1} = 2y_1 \Re(-ix_i) = 2y_1 \Im(x_i) \qquad \text{[Math. 6]}$$

This allows us to detect the imaginary part of the amplitude $x_i$. Thus, by using two modulating signals out of phase (either on different circuits or at different times), both the real and imaginary parts of the amplitude at a particular frequency can be extracted by the mixing sensor block 100. In other words, the absolute amplitude and the phase angle of a particular frequency component of the sensed signal on the sensing input line 101 can be extracted.

Figure 2:
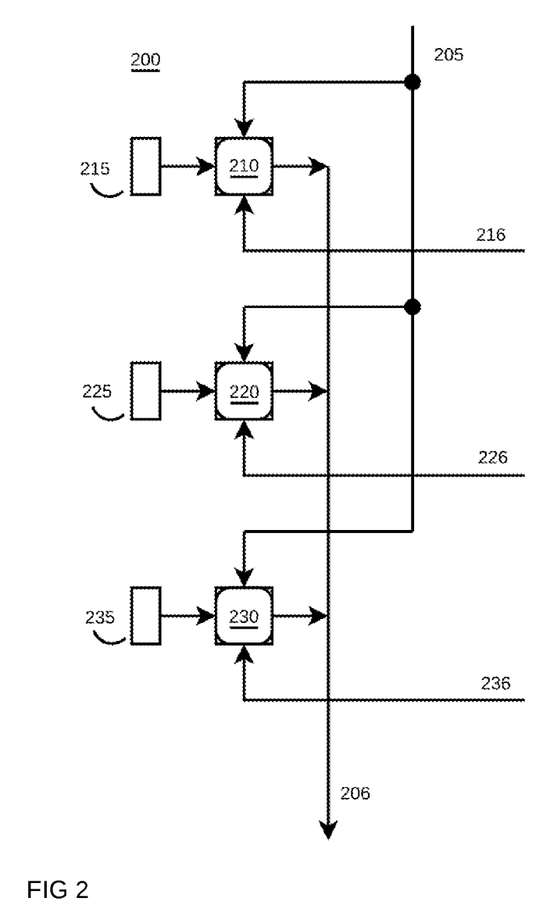
FIG. 2 illustrates a system sensing signals from multiple electrodes according to an embodiment.

FIG. 2 illustrates a system 200 sensing signals from multiple electrodes according to an embodiment.

Multiple electrodes 215, 225, 235 are electrically connected to the sensing input line of multiple mixing sensor blocks 210, 220, 230 respectively. A modulating signal source 205 provides the modulating signal to the mixing sensor blocks 210, 220, 230. Separate selection signals 216, 226, 236 are provided as signals to the selection input line of the mixing sensor blocks 210, 220, 230 respectively. The output lines of multiple mixing sensor blocks 210, 220, 230 are tied together to a single output signal line 206.

Even though the system is depicted as having three electrodes and three mixing sensor blocks, it may have a plurality of electrodes and corresponding mixing sensor blocks.

The same modulating signal (from the modulating signal source 205) is mixed with the various electrode signals in the mixing sensor blocks 210, 220, 230. A single selection signal is asserted at a particular time, thus creating a voltage output from one of the mixing sensor blocks 210, 220, 230 as selected. This voltage output is present on the output signal line 206. This output may be sensed using an ADC.

Over time, the modulating signal from modulating signal source 205 may be changed to various signal frequencies and/or phases. In an embodiment, the shape of the modulating signal is a sinusoidal. In another embodiment, the shape of the modulating signal is a square wave.

Figure 3:
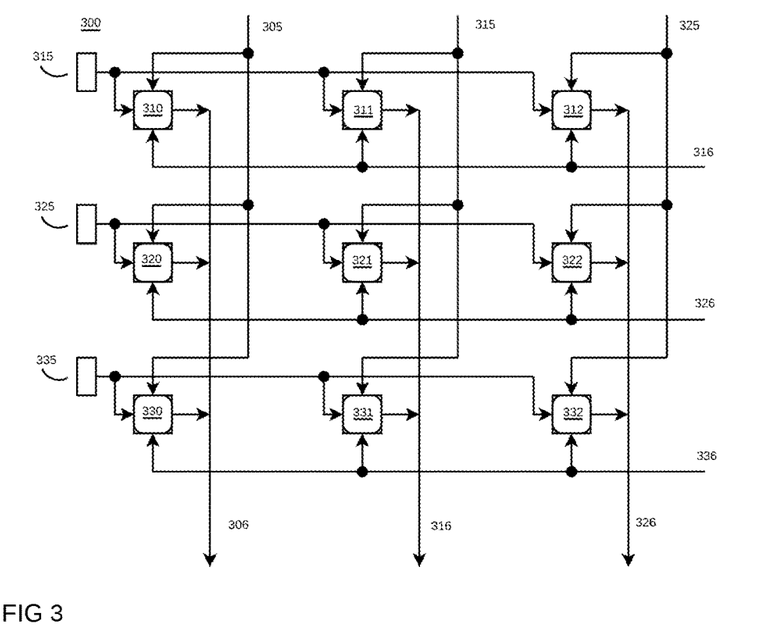
FIG. 3 illustrates a system sensing signals from multiple electrodes using multiple modulating signals according to an embodiment.

FIG. 3 illustrates a system 300 sensing signals from multiple electrodes using multiple modulating signals according to an embodiment.

A multiple of modulating signals from signal sources 305, 315, 325 are provided to the entire apparatus. Signal from each electrode from a plurality of electrodes 315, 325, 335 is connected to a plurality of mixing sensor blocks, one mixing sensor block for each pair of electrode and signal source. Selection signals 316, 326, 336 enable various mixing sensor blocks to produce output. For example, the selection signal 316 enables the mixing sensor blocks 310, 311, 312, all corresponding to the electrode 315, so that the mixing sensor blocks produce output corresponding to the signal of electrode 315 mixed with signals from signal sources 305, 315, 325 respectively to produce outputs on the output lines 306, 316 and 326 at the same time. Each of the output lines may be connected to a dedicated ADC, or the output lines may further be multiplexed onto the ADCs. Other combinations of enabling the mixing sensor blocks can be imagined as well.

Similarly, there are mixing sensor blocks 320, 321, 322 for electrode 325 and mixing sensor blocks 330, 331, 332 for electrode 335. Even though 3 electrodes and three modulating signals are depicted, any plurality of electrodes and any plurality of modulating signals may be provided in the system of the present invention. In an embodiment, some of the modulating signals are 90 degrees out of phase (but of the same frequency) as other modulating signals. This allows detection of real and imaginary phase components as described about with reference to FIG. 1.

Figure 4:
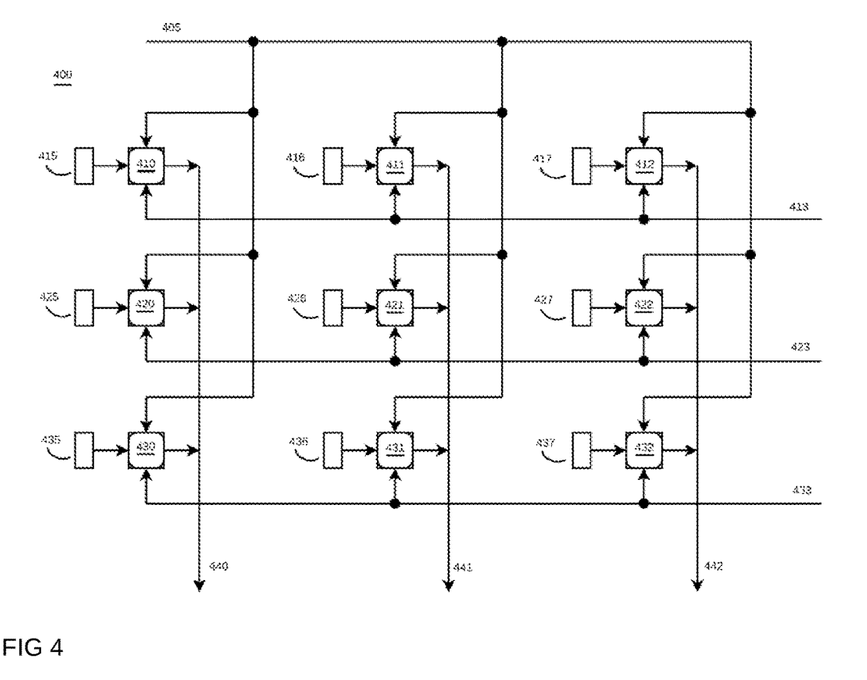
FIG. 4 illustrates a system sensing signals from multiple electrodes arranged in a matrix according to an embodiment.

FIG. 4 illustrates a system 400 sensing signals from multiple electrodes arranged in a matrix according to an embodiment.

Electrodes 415, 416, 417, 425, 426, 427, 435, 436, 437 are arranged in a matrix comprising rows and columns. Depending on the topology required of the physical electrodes, some of the electrodes in such a matrix may be missing. In an embodiment, the physical electrodes are arranged in a geometric matrix as well. In another embodiment, physical electrodes are arranged in a geometric structure which is regular, such as a hexagonal (honeycomb) pattern, and the electrical arrangement is correspondingly that of a matrix of rows and columns. In yet another embodiment, the physical electrodes are not arranged in a matrix, but the circuit is electrically arranged in a matrix as shows.

The electrodes 415, 416, 417, 425, 426, 427, 435, 436, 437 are connected as sensing inputs to corresponding mixing sensor blocks 410, 411, 412, 420, 421, 422, 430, 431, 432. All these mixing sensor blocks are given the same modulating signal 405 as modulating input. In an embodiment, more than one modulating signals may be present as described with reference to FIG. 3, and there may be correspondingly more than one mixing sensor blocks corresponding to each modulating signal. In an embodiment, two modulating signals are provided, of the same frequency but 90 degrees out of phase. Such signals may be sinusoidal signals or square waves.

A row selection signal 413 is provided as the selection input line to mixing sensor blocks 410, 411, 412 corresponding to the row of electrodes 415, 416, 417. If the row selection signal 413 is asserted, the mixing sensor blocks 410, 411, 412 will produce voltage output corresponding to the sensed mixed (modulated) information from the row of electrodes 415, 416, 417 onto the output lines 440, 441, 442. The output lines may have ADCs on each of them, or may further be multiplexed onto the ADCs. The output lines correspond to columns of electrodes.

If more than one modulating signals are provided, a single row selection signal may select all mixing sensor blocks of corresponding to all electrodes in a row, and all modulating signals. There will be output lines corresponding to each combination of electrode column and modulating signal.

If many ADCs are provided at the output lines they may be advantageously clubbed together in various ways to reduce the circuitry required. For example, a single ramp signal and clock signal may be provided across all the ADCs, and the ADCs individually compare the ramp signal to the signal on the corresponding output line (the output line is the input to the ADC), and when the comparison changes value, they will lock the count being counted up in a corresponding counter.

In another embodiment, the each ADC has a comparator and a capacitor that stores a voltage to be compared. A running voltage is provided on a global line, which takes values K/2, K/4, K/8, and so forth up to K/(2^k)) where K is a reference voltage and k is the bit depth. This global line provides this voltage to all ADCs. Each ADC compares the voltage at its input (the voltage on the corresponding output line) to the sum of the voltages on the global line and the voltage stored in the capacitor. If the input voltage is higher, a 1 bit is output, and the summed voltage is fed back to the capacitor. If the input voltage is lower, a 0 bit is output and the capacitor maintains its original voltage. In this way, the ADC may complete the conversion in k steps. In another embodiment, the capacitor is initially set to the voltage to be converted; and if a incoming global line voltage is smaller than the capacitor voltage, a '1' is output and the global line voltage is subtracted from the capacitor voltage and fed back to the capacitor voltage, else a '0' is output and the capacitor voltage is maintained.

Figure 5:
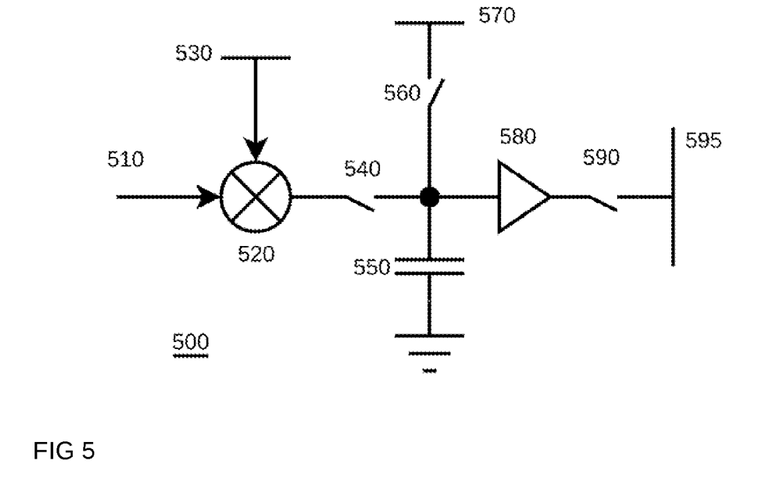
FIG. 5 illustrates a schematic of a mixing sensor block according to an embodiment.

FIG. 5 illustrates a schematic of a mixing sensor block 500, according to an embodiment.

A sensing input line 510 connects to an electrode (not shown). A modulating input line 530 brings in a modulating signal. The signal mixer 520 mixes the signal on the sensing input line 510 with the signal on modulating input line 530 by combining them non-linearly. The output of the signal mixer 520 is connected to an integrating circuit element 550 (such as a capacitor) through an optional transfer gate 540 which may be controlled by a transfer input signal. Closing the transfer gate 540 starts integrating the output of the signal mixer 520. The charge (or signal) accumulated in the integrating circuit element 550 may be reset to a reset voltage by asserting a reset input signal which connects the integrating circuit element 550 to the reset voltage line 570 through the reset gate 560. The output voltage of the integrating circuit element 550 is fed through a buffer 580 and an output gate 590 to an output line 595. When the output gate 590 is closed, it outputs the voltage at the integrating circuit element 550 onto the output line 595. When the output gate 590 is open, it presents a high impedance to the output line 595. In this way, the output line 595 may be shared between many mixing sensor blocks. The buffer 580 acts as a voltage follower and protects the signal stored in the integrating circuit element 550 from degradation, as the signal is output on the output line 595. It may also be used to boost or amplify the signal.

Figure 6:
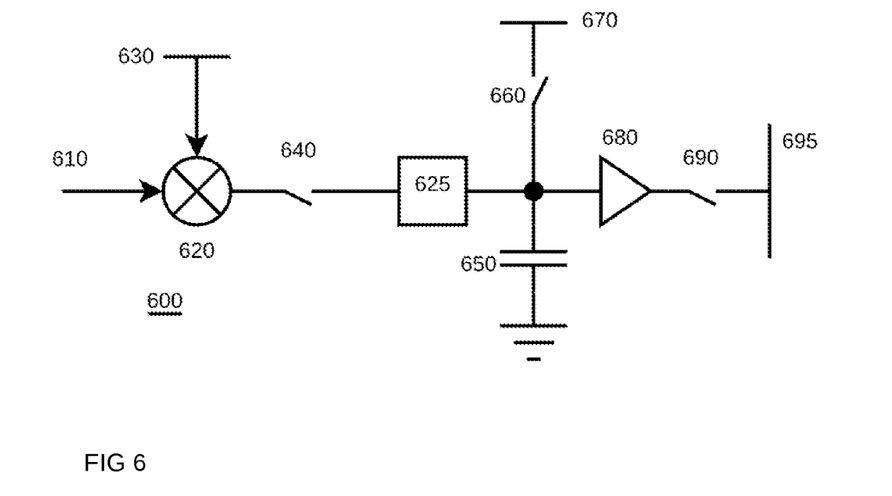
FIG. 6 illustrates a schematic of a mixing sensor block having a filter, according to an embodiment.

FIG. 6 illustrates a schematic of a mixing sensor block 600 having a filter, according to an embodiment.

A signal mixer 620 mixes the signal on the sensing input line 610 with the signal on modulating input line 630 by combining them non-linearly. The output of the signal mixer 620 is connected to an integrating circuit element 650 through a transfer gate 640 and a frequency selective filter 625. Closing the transfer gate 640 starts integrating the filtered output of the signal mixer 620. In series with the transfer gate 650 (or in place of it), a filter 625 is used to select a narrow band of frequencies. The narrow band of frequencies may be a base band (DC), or another narrow band of frequencies which may be then rectified to convert them to a DC signal. In an embodiment, the integrating circuit element 650 (which may be a capacitor) is itself the filter 625, which keeps the DC component and rejects the AC component.

The charge (or signal) accumulated in the integrating circuit element 650 may be reset to a reset voltage by asserting by connecting the integrating circuit element 650 to the reset voltage line 670 through the reset gate 660. The output voltage of the integrating circuit element 650 is fed through a buffer 680 and an output gate 690 to an output line 695.

Figure 7:
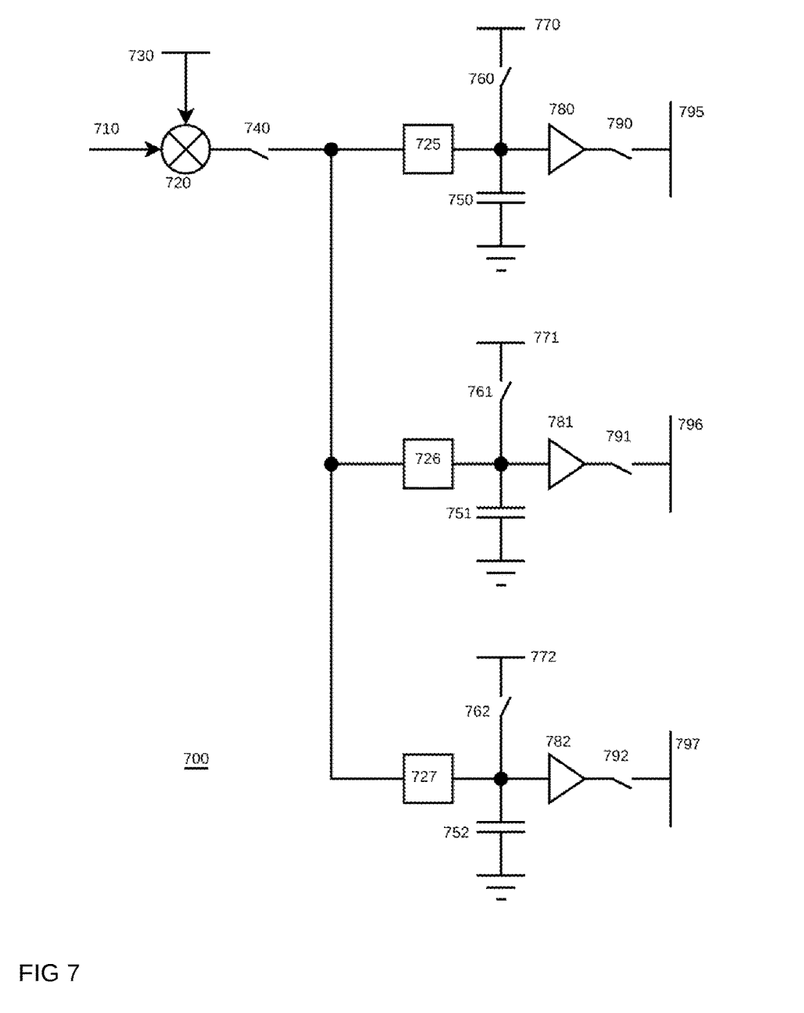
FIG. 7 illustrates a schematic of a mixing sensor block having multiple filters, according to an embodiment.

FIG. 7 illustrates a schematic of a mixing sensor block 700 having multiple filters, according to an embodiment.

A signal mixer 720 mixes the signal on the sensing input line 710 with the signal on modulating input line 730 by combining them non-linearly. The output of the signal mixer 720 is connected to various integrating circuit element 750, 751 and 752 through a transfer gate 740 and frequency selective filters 725, 726 and 727. Closing the transfer gate 740 starts integrating the filtered output of the signal mixer 720, as filtered through various filters. Each frequency selective filter 725, 726 and 727 selects a narrow band of frequencies to pass, and further may rectify these narrow band of frequencies to the base band, to be integrated by the corresponding integrating circuit elements 750, 751 752.

The charge (or signal) accumulated in the integrating circuit elements 750, 751, 752 may be reset to a reset voltage by closing the reset gates 760, 761, 762. The output voltage of the integrating circuit elements 750, 751, 752 are fed through buffers 780, 781, 782 and output gates 790, 791, 792 to output lines 795, 796, 797. The various reset gates may be controlled together, as may be the output gates.

Figure 8:
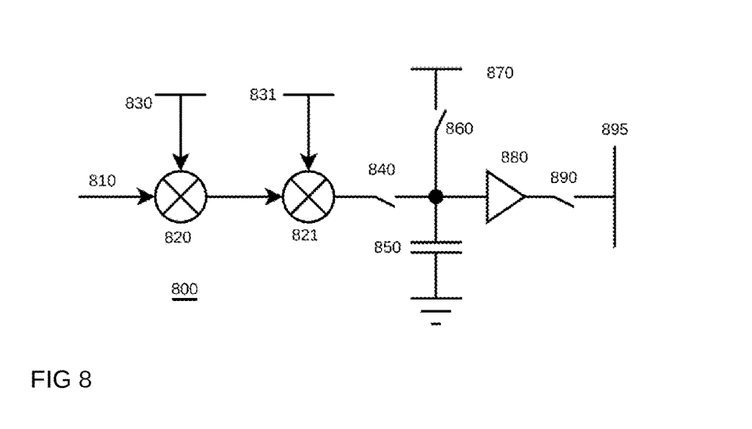
FIG. 8 illustrates a schematic of a mixing sensor block having two mixers, according to an embodiment.

FIG. 8 illustrates a schematic of a mixing sensor block 800 having two mixers, according to an embodiment.

A sensing input line 810 connects to an electrode (not shown). A modulating input line 830 brings in a modulating signal and another modulating input line 831 brings in another modulating signal. In an embodiment, the modulating signal on the modulating signal line 830 is of a high frequency (close to the frequency to be detected), whereas that on the modulating signal line 831 is of an intermediate frequency (between the frequency to be detected and DC). The signal mixer 820 mixes the signal on the sensing input line 810 with the signal on modulating input line 830 by combining them non-linearly. This produces a signal, one of whose components is an intermediate frequency signal which may be selectively passed to the next stage. The signal mixer 821 further mixes this intermediate frequency detected signal with the intermediate frequency modulating signal to produce a base band signal. The output of the signal mixer 821 is connected to an integrating circuit element 850 (such as a capacitor) through an optional transfer gate 840. Closing the transfer gate 840 starts integrating the output of the signal mixer 821. The charge (or signal) accumulated in the integrating circuit element 850 may be reset to a reset voltage by asserting by connecting the integrating circuit element 850 to the reset voltage line 870 through the reset gate 860. The output voltage of the integrating circuit element 850 is fed through a buffer 880 and an output gate 890 to an output line 895.

In an embodiment, multiple lines carry high frequency modulating signals (of different frequencies) and intermediate frequency modulating signals (of different frequencies). Each pair of high frequency and intermediate frequency modulating signals produces a different mixer output. Each electrode is connected to many mixing sensor blocks, one for each pair of modulating signals. Thus, many frequencies may be simultaneously sensed. The electric current entering the body is also created to have these same frequencies.

Figure 9:
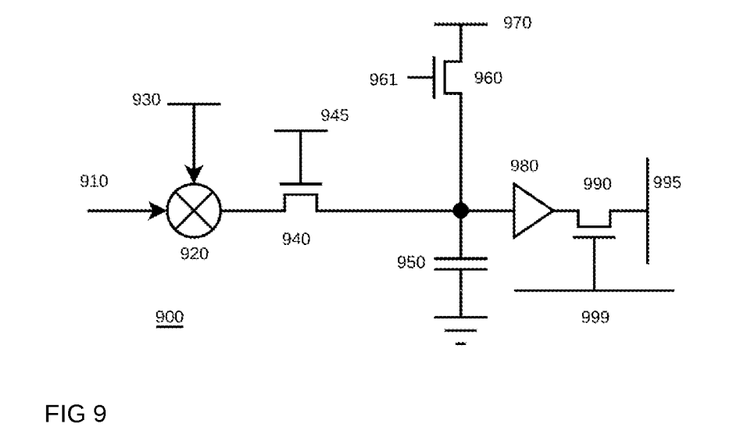
FIG. 9 illustrates a schematic of a mixing sensor block that uses transistors as switches, according to an embodiment.

FIG. 9 illustrates a schematic of a mixing sensor block 900 that uses transistors as switches, according to an embodiment.

A signal mixer 920 mixes the signal on the sensing input line 910 with the signal on modulating input line 930 by combining them non-linearly. The output of the signal mixer 920 is connected to an integrating circuit element 950 (such as a capacitor) through an optional transfer gate transistor 940 which is controlled by a transfer input signal 945. In an embodiment, one or more of the transistors referred to in this disclosure are CMOS transistors. Asserting the transfer input signal 945 starts integrating the output of the signal mixer 920. The charge (or signal) accumulated in the integrating circuit element 950 may be reset to a reset voltage by asserting a reset input signal 961 which connects the integrating circuit element 950 to the reset voltage line 970 through the reset gate transistor 960. The output voltage of the integrating circuit element 950 is fed through a buffer 980 and an output gate transistor 990 (that is controlled by a selection input line 999) to an output line 995. When the selection input line 999 is asserted, the output gate transistor 990 outputs the voltage at the integrator onto the output line 995. The buffer 980 acts as a voltage follower and protects the signal stored in the integrating circuit element 950 from degradation.

Figure 10:
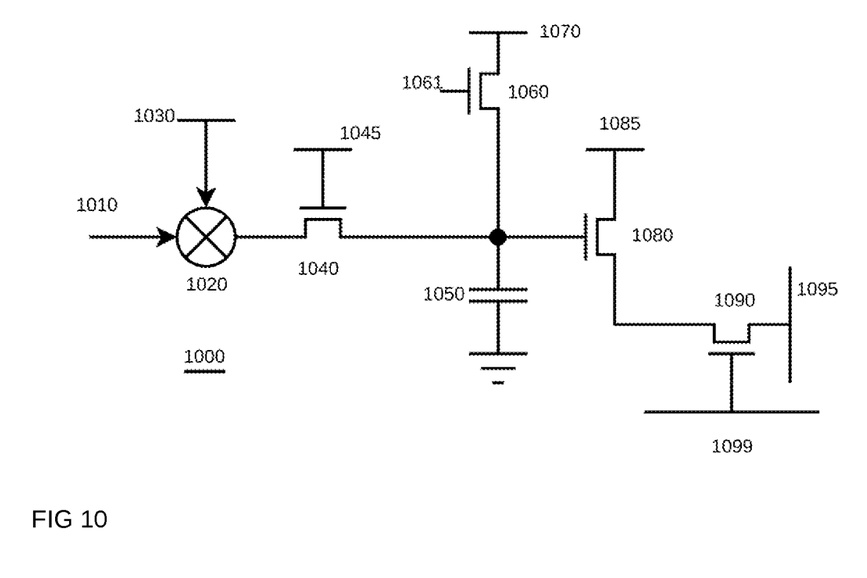
FIG. 10 illustrates a schematic of a mixing sensor block that uses a transistor as buffer, according to an embodiment.

FIG. 10 illustrates a schematic of a mixing sensor block 1000 that uses a transistor as buffer, according to an embodiment.

A signal mixer 1020 mixes the signal on a sensing input line 1010 with the signal on a modulating input line 1030 by combining them non-linearly. The output of the signal mixer 1020 is connected to an integrating circuit element 1050 (such as a capacitor) through an optional transfer gate transistor 1040 which may be controlled by a transfer input signal 1045. Asserting the transfer input signal 1045 starts integrating the output of the signal mixer 1020. The charge (or signal) accumulated in the integrating circuit element 1050 may be reset to a reset voltage by asserting a reset input signal 1061 which connects the integrating circuit element 1050 to the reset voltage line 1070 through the reset gate transistor 1060. The output voltage of the integrating circuit element 1050 is fed through a buffer transistor 1080 and an output gate 1090 (controlled by a selection input line 1099) to an output line 1095. When the selection input line 1099 is asserted, the output gate transistor 1090 outputs the voltage at the integrator onto the output line 1095. The buffer transistor 1080 acts as a voltage follower and protects the signal stored in the integrating circuit element 1050 from degradation.

Figure 11:
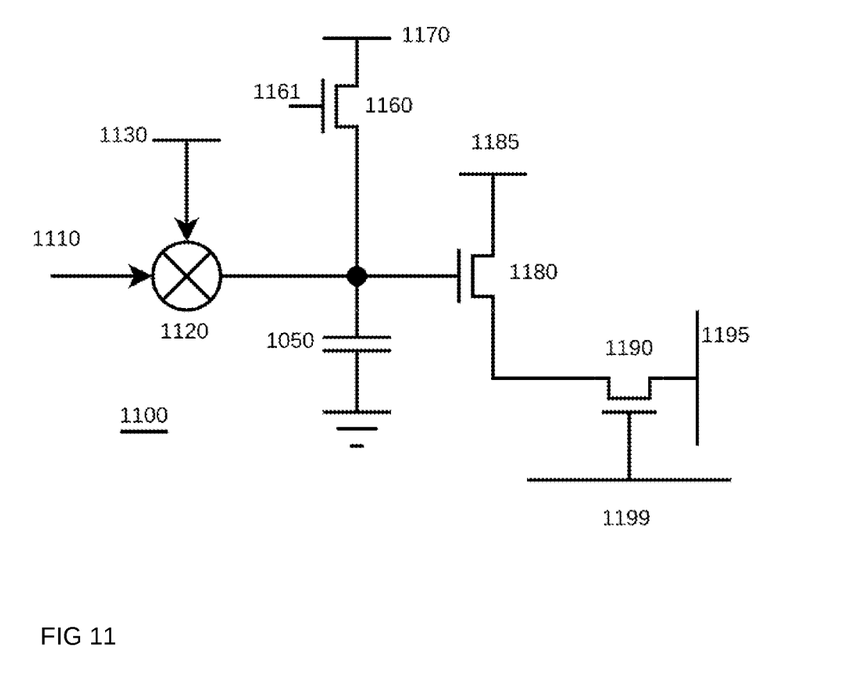
FIG. 11 illustrates a schematic of a mixing sensor block without a transfer gate, according to an embodiment.

FIG. 11 illustrates a schematic of a mixing sensor block 1100 without a transfer gate, according to an embodiment.

A signal mixer 1120 mixes the signal on a sensing input line 1110 with the signal on a modulating input line 1130 by combining them non-linearly. The output of the signal mixer 1120 is connected to an integrating circuit element 1150 (such as a capacitor). Since there is no transfer gate, this connection is permanent and integration is always being performed. The integration may only be reset (as described below), but may not be stopped. The charge (or signal) accumulated in the integrating circuit element 1150 may be reset to a reset voltage by asserting a reset input signal 1161 which connects the integrating circuit element 1150 to the reset voltage line 1170 through the reset gate transistor 1160. The output voltage of the integrating circuit element 1150 is fed through a buffer transistor 1180 and an output gate transistor 1190 (controlled by an selection input line 1199) to an output line 1195. When the selection input line 1199 is asserted, the output gate transistor 1190 outputs the voltage at the integrator onto the output line 1195. The buffer transistor 1180 acts as a voltage follower and protects the signal stored in the integrating circuit element 1150 from degradation.

Figure 12:
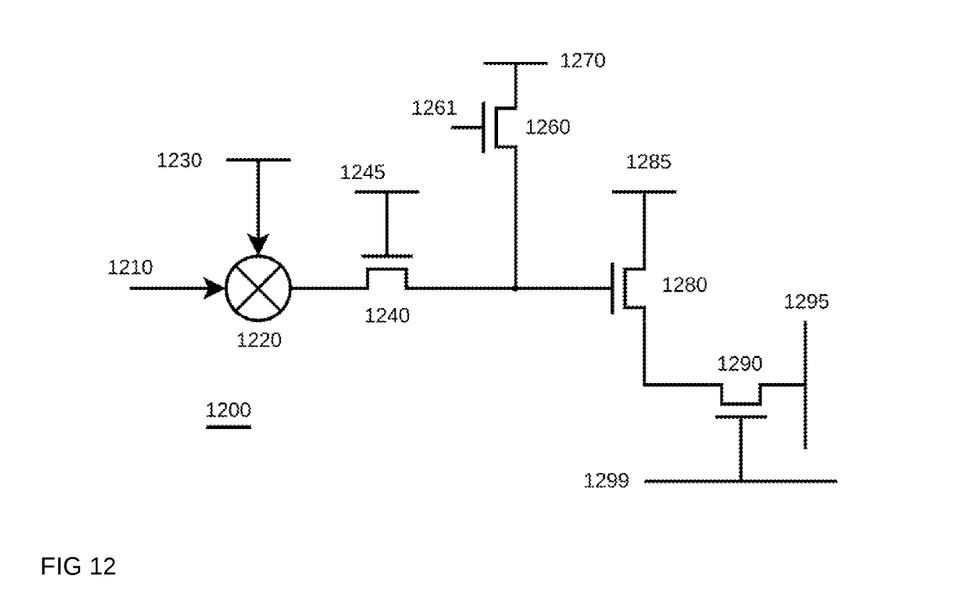
FIG. 12 illustrates a schematic of a mixing sensor block with an implicit integrating element, according to an embodiment.

FIG. 12 illustrates a schematic of a mixing sensor block 1200 with an implicit integrating element, according to an embodiment.

A signal mixer 1220 mixes the signal on a sensing input line 1210 with the signal on a modulating input line 1230 by combining them non-linearly. The output of the signal mixer 1220 is connected to an integrating circuit element through an optional transfer gate transistor 1240 which may be controlled by a transfer input signal 1245. The integrating circuit element is not an explicit, separate circuit element in this embodiment. The integrating circuit element is the gate capacitance of the buffer transistor 1280, the junction-to-junction (source-to-drain) capacitance of the reset gate transistor 1260 (while it is off) and the source-to-gate capacitance of the transfer gate transistor 1240.

Asserting the transfer input signal 1245 starts integrating the output of the signal mixer 1220. The charge (or signal) accumulated in the integrating circuit element may be reset to a reset voltage by asserting a reset input signal 1261 which connects the charge-accumulating node of the integrating circuit element to the reset voltage line 1270 through the reset gate 1260. The output voltage of the integrating circuit element is fed through a buffer transistor 1280 and an output gate 1290 (controlled by an selection input line 1299) to an output line 1295.

Figure 13:
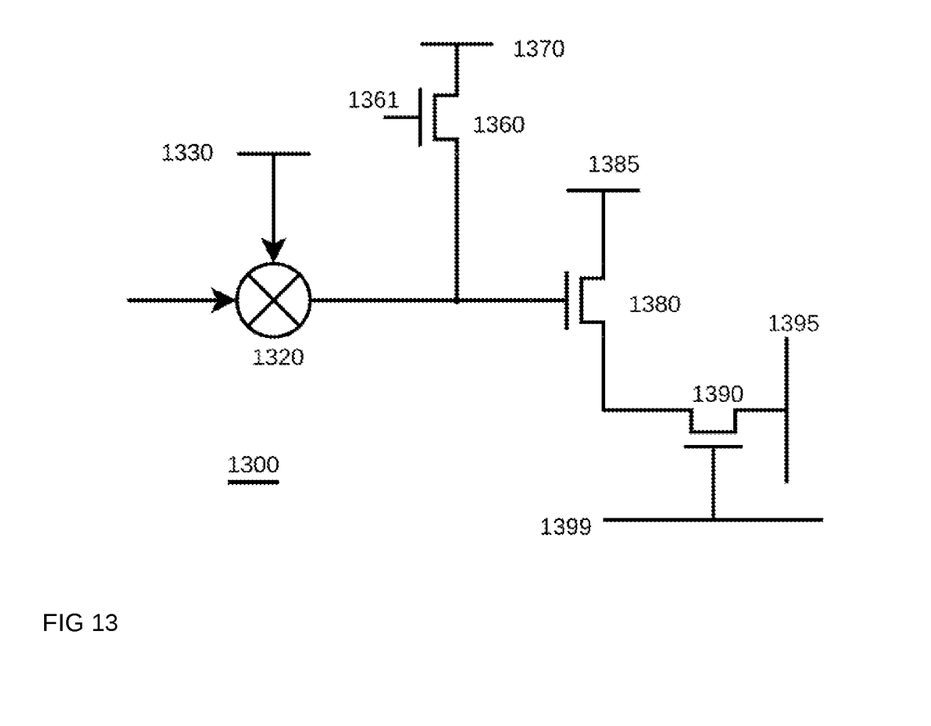
FIG. 13 illustrates a schematic of a mixing sensor block with an implicit integrating element and no transfer gate, according to an embodiment.

FIG. 13 illustrates a schematic of a mixing sensor block 1300 with an implicit integrating element and no transfer gate, according to an embodiment.

A signal mixer 1320 mixes the signal on a sensing input line 1310 with the signal on a modulating input line 1330 by combining them non-linearly. The output of the signal mixer 1320 is connected to an integrating circuit element. The integrating circuit element is not an explicit, separate circuit element in this embodiment. The integrating circuit element is the gate capacitance of the buffer transistor 1380 and the junction-to-junction (source-to-drain) capacitance of the reset gate transistor 1360 (while it is off). The charge (or signal) accumulated in the integrating circuit element may be reset to a reset voltage by asserting a reset input signal 1361 which connects the charge-accumulating node of the integrating circuit element to the reset voltage line 1370 through the reset gate 1360. The output voltage of the integrating circuit element is fed through a buffer transistor 1380 and an output gate 1390 (controlled by a selection input line 1399) to an output line 1295.

Figure 14:
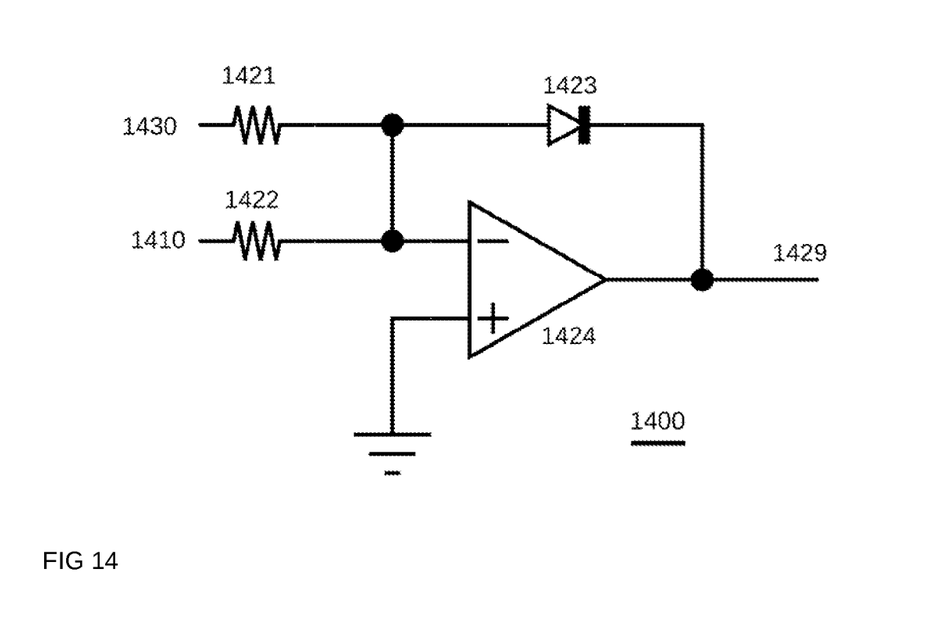
FIG. 14 illustrates a schematic of a mixer according to an embodiment.

FIG. 14 illustrates a schematic of a mixer 1400 according to an embodiment.

The mixer 1400 mixes signals 1410 and 1430 by combining them non-linearly. In an embodiment, the signal 1410 may be a signal from an electrode, and signal 1430 may be a modulating signal. Any circuit that combines them non-linearly may be used, such as various known signal multiplier circuits. In this embodiment, the circuit consists of resistors 1421 and 1422 feeding the two signals to the inverting terminal of a differential amplifier 1424, whose non-inverting terminal is grounded. The inverting terminal is also connected to the output of the differential amplifier 1424 through a diode 1423. This has the effect of passing the sum of two signals through a non-linear function, in this case approximated as the logarithm. The output produced by the differential amplifier 1424 non-linearly combines the signals 1410 and 1430.

Figure 15:
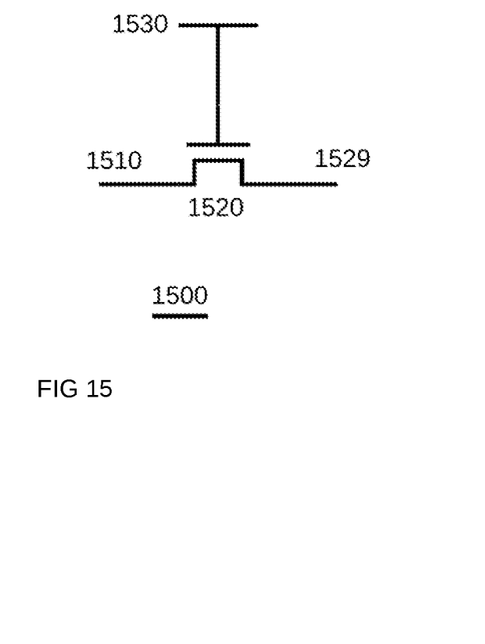
FIG. 15 illustrates a schematic of a mixer comprising a single transistor according to an embodiment.

FIG. 15 illustrates a schematic of a mixer 1500 comprising a single transistor according to an embodiment.

Signal 1510 from the electrode is given to one terminal (source or drain) of a transistor 1520 (that may be a CMOS transistor), and the modulating signal 1530 is given to the gate of the transistor 1520. The second terminal of the transistor 1520 is used as the output signal that non-linearly combines the two signals. If the input from the electrode is very weak, it may be beneficial to connect the input from the electrode to the gate, and the modulating signal 1530 to a terminal (source or drain) of the transistor.

Figure 16:
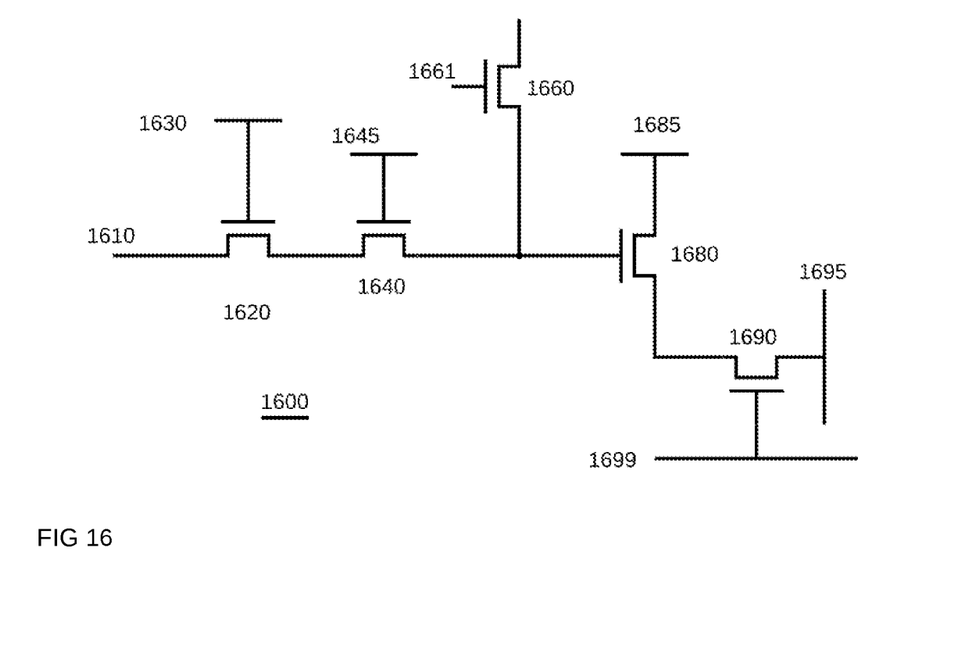
FIG. 16 illustrates a schematic of a mixing sensor block using transistors, according to an embodiment.

FIG. 16 illustrates a schematic of a mixing sensor block 1600 using transistors, according to an embodiment.

A sensing input line 1610 connects to an electrode (not shown). A modulating input line 1630 brings in a modulating signal. The signal mixing transistor 1620 mixes the signal on the sensing input line 1610 with the signal on modulating input line 1630 by combining them non-linearly. The output of the signal mixing transistor 1620 is connected to an integrating circuit element (such as a capacitor or implicit transistor capacitances) through an optional transfer gate transistor 1640 which may be controlled by a transfer input signal 1645. Asserting the transfer input signal 1645 starts integrating the output of the signal mixing transistor 1620. The charge (or signal) accumulated in the integrating circuit element may be reset to a reset voltage by asserting a reset input signal 1661 which connects the integrating circuit element to the reset voltage line 1670 through the reset gate 1660. The output voltage of the integrating circuit element is fed through a buffer transistor 1680 and an output gate transistor 1690 (controlled by a selection input line) 1699 to an output line 1695. When the selection input line 1699 is asserted, the output gate transistor 1690 outputs the voltage at the integrator onto the output line 1695. The buffer transistor 1680 acts as a voltage follower and protects the signal stored in the integrating circuit element 1650 from degradation.

Figure 17:
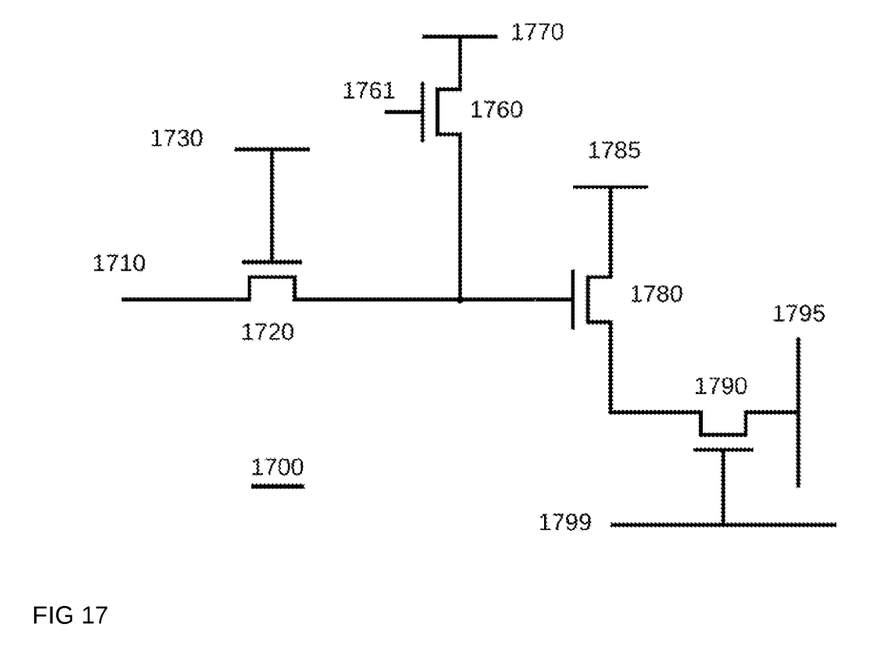
FIG. 17 illustrates a schematic of a mixing sensor block using transistors and no transfer gate, according to an embodiment.

FIG. 17 illustrates a schematic of a mixing sensor block 1700 using transistors and no transfer gate, according to an embodiment.

A sensing input line 1710 connects to an electrode (not shown). A modulating input line 1730 brings in a modulating signal. The signal mixing transistor 1720 mixes the signal on the sensing input line 1710 with the signal on modulating input line 1730 by combining them non-linearly. The output of the signal mixing transistor 1720 is connected to an integrating circuit element (such as a capacitor or implicit transistor capacitances). The charge (or signal) accumulated in the integrating circuit element may be reset to a reset voltage by asserting a reset input signal 1761 which connects the integrating circuit element to the reset voltage line 1770 through the reset gate 1760. The output voltage of the integrating circuit element is fed through a buffer transistor 1780 and an output gate transistor 1790 (controlled by a selection input line 1799) to an output line 1795. When the selection input line 1799 is asserted, the output gate transistor 1790 outputs the voltage at the integrator onto the output line 1795. The buffer transistor 1780 acts as a voltage follower and protects the signal stored in the integrating circuit element 1750 from degradation.

Figure 18:
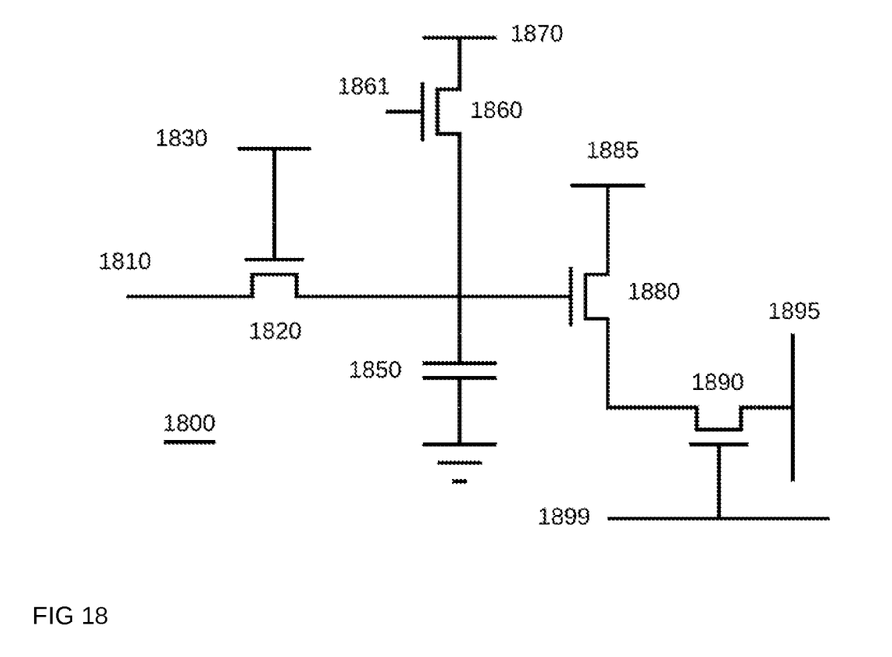
FIG. 18 illustrates a schematic of a mixing sensor block using transistors and capacitors, according to an embodiment.

FIG. 18 illustrates a schematic of a mixing sensor block 1800 using transistors and capacitors, according to an embodiment.

A sensing input line 1810 connects to an electrode (not shown). A modulating input line 1830 brings in a modulating signal. The signal mixing transistor 1820 mixes the signal on the sensing input line 1810 with the signal on modulating input line 1830 by combining them non-linearly. In an embodiment, the sensing input line 1810 is connected to the gate of the signal mixing transistor and the modulating input line 1830 is connected to the terminal; in another embodiment (shown), the sensing input line 1810 is connected to the terminal of the signal mixing transistor and the modulating input line 1830 is connected to the gate. The output of the signal mixing transistor 1820 is connected to a capacitor 1850 that acts as an integrating circuit element. The charge (or signal) accumulated in the integrating circuit element 1850 may be reset to a reset voltage by asserting a reset input signal 1861 which connects the capacitor 1850 to the reset voltage line 1870 through the reset gate 1860. The output voltage of the capacitor 1850 is fed through a buffer transistor 1880 and an output gate 1890 controlled by an selection input line 1899 to an output line 1895. When the selection input line 1899 is asserted, the output gate transistor 1890 outputs the voltage at the integrator onto the output line 1895.

Figure 19:
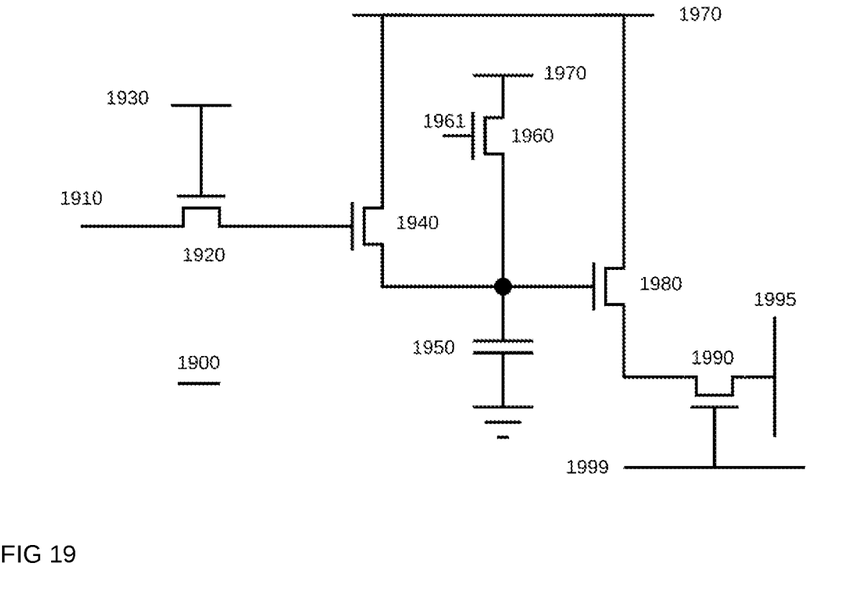
FIG. 19 illustrates a schematic of a mixing sensor block using two transistors, according to an embodiment.

FIG. 19 illustrates a schematic of a mixing sensor block 1900 using two transistors, according to an embodiment.

A sensing input line 1910 connects to an electrode (not shown). A modulating input line 1930 brings in a modulating signal. The signal mixing transistor 1920 mixes the signal on the sensing input line 1910 with the signal on modulating input line 1930 by combining them non-linearly. The output of the signal mixing transistor 1920 is connected to an integrating circuit element 1950 (such as a capacitor) through an optional buffer transistor 1940. The charge (or signal) accumulated in the integrating circuit element 1950 may be reset to a reset voltage by asserting a reset input signal 1961 which connects the integrating circuit element 1950 to the reset voltage line 1970 through the reset gate 1960. The output voltage of the integrating circuit element 1950 is fed through a buffer transistor 1980 and an output gate 1990 controlled by an selection input line 1999 to an output line 1995. Both the buffer transistors 1940 and 1980 may be connected to the same voltage source 1985. When the selection input line 1999 is asserted, the output gate transistor 1990 outputs the voltage at the integrator onto the output line 1995. The buffer transistor 1980 acts as a voltage follower and protects the signal stored in the integrating circuit element 1950 from degradation.

Figure 20:
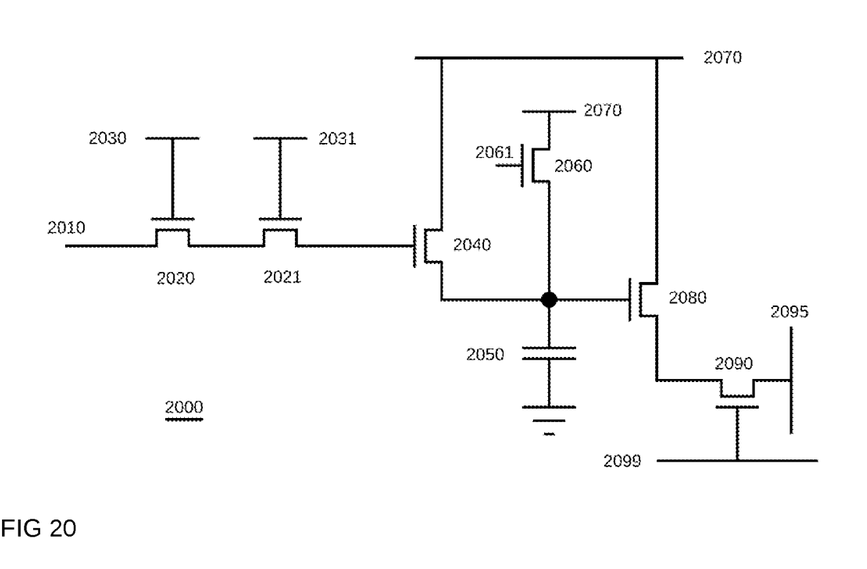
FIG. 20 illustrates a schematic of a mixing sensor block having multiple signal mixing transistors, according to an embodiment.

FIG. 20 illustrates a schematic of a mixing sensor block 2000 having multiple signal mixing transistors, according to an embodiment.

A sensing input line 2010 connects to an electrode (not shown). A modulating input line 2030 brings in a modulating signal. The signal mixing transistor 2020 mixes the signal on the sensing input line 2010 with the signal on modulating input line 2030 by combining them non-linearly. The output of the signal mixing transistor 2020 is connected to another signal mixing transistor 2021 which combines the signal with the second modulating signal on the modulating input line 2031. The output of the signal mixing transistor is connected to an integrating circuit element 2050 (such as a capacitor) through an optional transfer gate (not shown) and an optional buffer transistor 2040. The charge (or signal) accumulated in the integrating circuit element 2050 may be reset to a reset voltage by asserting a reset input signal 2061 which connects the integrating circuit element 2050 to the reset voltage line 2070 through the reset gate 2060. The output voltage of the integrating circuit element 2050 is fed through a buffer transistor 2080 and an output gate 2090 (controlled by a selection input line 2099) to an output line 2095. When the selection input line 2099 is asserted, the output gate transistor 2090 outputs the voltage at the integrator onto the output line 2095. The buffer transistor 2080 acts as a voltage follower and protects the signal stored in the integrating circuit element 2050 from degradation. Both the buffer transistors may be connected to the same voltage source 2085, or to separate voltage sources.

Other Embodiments

An AC electric current of a particular frequency is introduced into the body to be sensed. In an embodiment, a superposition of multiple frequencies is introduced simultaneously into the body. This causes voltages to be produced at various points of the surface of the body. Electrodes are connected to various points of the surface of the body. These electrodes pick up the amplitudes and phases of the particular frequencies specifically introduced into the body, as described in various embodiments above. This sensing is done simultaneously across multiple electrodes. These electrodes may number in the hundreds, or may be a matrix of electrodes numbering in the thousands. Simultaneous sensing across a plurality of electrodes achieves speeds of acquisition which are impossible when sensing only across one pair of electrodes at a time (as is usually the norm).

The readout signal may be provided as more than one signal, for example a row and a column signal, assertion of both of which will cause the readout to take place. In this way, a 2D array of electrodes can be managed one electrode at a time. Alternatively, only a row signal may be provided, causing simultaneous readout of an entire row, requiring an A-to-D converter per column, but faster readout. In this way, we can reduce the number of A-to-D converters to just one (if only one electrode is read out at a time) or equal to the number of logical columns of electrodes (number of electrodes in a row). Other number of A-to-D converters are possible as well, by appropriate wiring.

Assertion of the transfer signal (enabling transfer gates) may be performed for the entire matrix of electrodes at a time, or for a row at a time, rolling from one end of the matrix to the next. The readout, may be synchronized in such a way that the most exposed row of electrodes is being read while transfer is disabled, immediately after which the row charges are reset and transfer into the integrators is started again.

In an embodiment, the charge recorded at each electrode, after the exposure time is complete, is transferred to a separate readout capacitor or semiconductor device that can store charge, so that the next exposure period can start sooner. Alternatively, data may be read one row at a time, and the exposures are also reset row-wise. A row-wise or device-wide reset signal is provided so that the stored charge may be reset so that a new measurement can start after the charge is reset or drained. Implicit or explicit integration time control is provided row-wise or device-wide which decides if the capacitor is charging or lying idle.

In an embodiment, there may be a linear or non-linear relation between the sensed levels and the actual AC amplitude and phase, which is carefully calibrated.

In an embodiment, instead of measuring various voltages, various currents are measured. This measurement may be performed by measuring voltages across known resistors. The known resistors may be variable resistors as described below.

In an embodiment, the same electrodes that are used for sensing may also be used for setting up the AC current that moves through the body being sensed. The AC current may be setup as being between two specific electrodes, or more than two electrodes may participate in the process. For example, spatial patterns may be created such as the 2D Fourier basis (real part and imaginary part produced separately at separate times). In this way, current is not concentrated at a single electrode, but still the entire vector space of possible current settings is traversed.

In an embodiment, these spatial patterns are changed gradually (compared to the AC frequency itself), not abruptly. The sensing may be done as before in multiple frames, or the gradual shift in the spatial pattern may itself be used as additional modulation for the electrode measurement circuit to record more than two values per electrode, and then finally read everything out.

In an embodiment, many electrodes are provided in a line, 2D matrix, honeycomb arrangement etc. Each electrode is a rod with a hemispherical tip, with at least the tip being conductive. The tip and rod may have another shape such as a hexagonal prismatic rod with a filleted hexagonal cap, etc. These rods are individually spring loaded, meaning they can move in and out of a base on which they are mounted. When these rods are pressed against a body, they will conform to the contours of the body, and each will make electrical contact with the body. Measurement of how much each rod is pushed may be provided, e.g. using proximity sensors, measurements using rheostats (position dependent resistances), measurements using strain gauges, etc. The resistance measurements transducing how much each rod is pushed may be transmitted over the same lines as the electrode measurements are. Each rod tip may be broken into multiple electrodes, with 2, 3, 4, 6 side electrodes and zero or one center electrode. This will allow an accurate measurement of the local impedance seen by the electrode (contact impedance, skin impedance, etc.).

The 2D matrix or honeycomb of electrodes may be arranged in a flat arrangement which conforms to a certain extent to the body being measured. This flat arrangement may be placed horizontally as a bed for a patient or object to lie on, or as the backrest of a chair or a wall etc. More than one such panels may be used to surround the object being measured. The arrangement may not be flat but some other shape such as a cylinder or even a wearable vest or other piece of clothing.

In an embodiment, the contact between the electrodes and the body being measured is direct. In another embodiment, a conductive gel is placed on each electrode, or a single conducting gel is spread on the entire body. The tips of the electrodes may be disposable, or may be a single disposable sheet.

In an embodiment, dynamic resistance circuits (resistances that can be set to various values) are present at every electrode. A fixed AC voltage waveform is applied through this resistance to the body. Resistance values are known, and voltage amplitude and phase is measured. In another embodiment, dynamically set voltage patterns are applied to the body through fixed resistances. The voltages at the non-driven ends of the resistances (which are also the voltages seen by the electrodes) are sensed by the electrode circuits. From knowledge of the resistance and the voltages at its two ends (one being set and the other being measured by the system), the current through the electrode can be calculated. Thus both the current and voltage at every electrode is known.

In an embodiment, spatial patterns of electrode excitation may be set up by setting each electrode in one of a finitely many states. The states could be (a) current drive +ve
(b) current drive −ve
(c) zero current (floating electrode)

(e) current drive +90 deg
(f) current drive −90 deg
(g) voltage drive +ve
(h) voltage drive −ve
(i) voltage drive ground
(j) voltage drive +90 deg
(k) voltage drive −90 deg In various embodiments, various subsets of the above states may be employed. In particular, the following combinations to be provided in particular embodiments:

(g), (i)
(g), (i), (c)
(g), (h), (i)
(g), (h), (c)
(g), (h), (i), (c)
(g), (h), (i), (j), (k), (c)

Global AC voltage lines (+ve signal, −ve signal, +90 deg phase shifted, −90 deg phase shifted, ground) may be provided to each electrode circuit, and a multiplexer chooses one of these signals (or none, to float the electrode) to connect to the electrode that connects to the body to be measured. Furthermore, one or more than one of these signals may be passed through fixed or variable resistors to produce newer effective phases and amplitudes. The global lines may be voltage drives or current drives. In the case of current drives, the electrodes are still connected on a single current drive in parallel, thus producing the same voltage across all electrodes connected to a single current drive. The current drive helps to regulate the current flowing into the body, which may be important for regulating the amount of current entering the body being sensed, for reasons of safety. It is also possible that after creating a voltage signal using the above techniques at each electrode, a voltage-to-current converter (amplifier) is used so that each electrode is an independent current drive. This will ensure that safety regulations regarding current density are met.

In an embodiment the spatial excitation patterns which are set up are spatially periodic patterns. Some patterns have a smaller spatial period and others have a larger spatial period. The periodic pattern may comprise of a unit that is repeated, where the unit itself has some excitations surrounded by a region that is electrically floating. (The electrically floating region can still sense voltage). In such situations, each repeating unit may be approximately thought to produce a response that is independent of other units. Thus the sampling speed is improved. Smaller repeating units will provide information about shallower objects whereas larger repeating units will provide information of deeper objects.

In an embodiment, the modulating signal amplitude and phase changes due to unavoidable circuit reasons at various mixing sensor blocks. (Frequency does not change.) This variation in amplitude and phase across the system is carefully calibrated and then corrected for while the signal is being digitally processed.

INDUSTRIAL APPLICABILITY

Electrical impedance tomography may be used for medical or biological imaging (where the conductive body is the human/biological body, and information to be gained about the body includes information about internal organs, etc.), geophysical/ground surveys (where the conductive body is the Earth, and information to be gained about the body includes information about presence of water, oil, minerals, etc.) and non-destructive testing of machines, engineered bodies, civil constructions or materials (where the conductive body is the machine, civil structure/building, material sample etc., and information to be gained includes information about interior material presence, cracks, interior structure, etc.). It may also be used in applications such as archeology, forensic science, security, etc. where knowledge of the interior of a body without accessing the interior of the body is important.

I claim:

1. A system comprising a plurality of electrodes, each electrode electrically connected to one or more mixing sensor blocks, each mixing sensor block connected to at least two modulating signals, a selection signal and an output electrical line wherein each mixing sensor block from the one or more mixing sensor blocks is configured to non-linearly mix an electrical signal from the electrode it is connected to with each modulating signal of the at least two modulating signals that it is connected to, to produce a modulated signal that is integrated, and to output a voltage corresponding to the integrated signal on the output electrical line when the selection signal is asserted, and wherein the two modulating signals are of distinct frequencies from each other.

2. The system of claim 1 further comprising multiple sets of modulating signals, wherein each electrode is connected to a plurality of mixing sensor blocks, each mixing sensor block of the plurality of mixing sensor blocks is connected to a specific modulating signal from each set of modulating signals of the multiple sets of modulating signals.

3. The system of claim 2 wherein each modulating signal from each set of modulating signals is a sinusoidal of a particular frequency.

4. The system of claim 2 further comprising at least one set of the multiple sets of modulating signals comprising at least one pair of modulating signals having the same frequency but phase-shifted with respect to each other by 90 degrees.

5. The system of claim 1 wherein each mixing sensor block resets the integrated signal when a reset signal is asserted.

6. The system of claim 1 wherein the electrodes are arranged in a matrix of rows and columns.

7. The system of claim 1 wherein the electrodes are arranged in a hexagonally packed or honeycomb structure.

8. The system of claim 1 wherein the electrodes are configured to be attached to a body being sensed and are capable of producing current that can enter the body being sensed.

9. The system of claim 8 wherein the current that can enter the body being sensed comprises current that is simultaneously of multiple frequencies.

10. The system of claim 1 wherein the electrical signal from the electrode is mixed with a first modulating signal, and the output of this mixing is mixed with a second modulating signal.

11. The system of claim 10 wherein the mixing of the electrode signal with the first modulating signal and the mixing of the output of this mixing with the second modulating signal is performed using a circuit having an operational amplifier and a diode, the circuit configured to pass a sum of the electrode signal and at least one of the modulating signals through the diode.

12. The system of claim 10 wherein the mixing of the electrode signal with the first modulating signal and the mixing of the output of this mixing with the second modulating signal is performed using a circuit having a transistor.

13. The system of claim 10 wherein the mixing of the electrode signal with the first modulating signal and the mixing of the output of this mixing with the second modulating signal is performed using a circuit having a plurality of transistors.

\* \* \* \* \*